United States Patent [19]
Lary

[11] Patent Number: 5,792,158
[45] Date of Patent: *Aug. 11, 1998

[54] UNIVERSITY DILATOR WITH EXPANDABLE INCISOR

[76] Inventor: Banning Gray Lary, 6371 SW. 87th Ter., Miami, Fla. 33143

[*] Notice: The term of this patent shall not extend beyond the expiration date of Pat. No. 5,697,944.

[21] Appl. No.: 743,716

[22] Filed: Nov. 6, 1996

Related U.S. Application Data

[63] Continuation-in-part of Ser. No. 559,415, Nov. 15, 1995, Pat. No. 5,697,944.

[51] Int. Cl.$^6$ ............................................. A61B 17/00
[52] U.S. Cl. ............................... 606/159; 606/170; 604/22
[58] Field of Search ................................ 606/1, 108, 159, 606/167, 170, 171, 180; 604/96; 128/898, 899

[56] References Cited

U.S. PATENT DOCUMENTS

| | | |
|---|---|---|
| 3,635,223 | 1/1972 | Klieman . |
| 3,990,453 | 11/1976 | Douvas et al. . |
| 4,273,128 | 6/1981 | Lary . |
| 4,465,072 | 8/1984 | Taheri . |
| 4,685,458 | 8/1987 | Leckrone . |
| 4,696,667 | 9/1987 | Masch . |
| 4,723,549 | 2/1988 | Wholey et al. . |
| 5,009,659 | 4/1991 | Hamlin et al. . |
| 5,100,425 | 3/1992 | Fischell et al. . |
| 5,156,610 | 10/1992 | Reger . |
| 5,196,024 | 3/1993 | Barath . |
| 5,320,634 | 6/1994 | Vigil et al. . |

FOREIGN PATENT DOCUMENTS 938977  6/1982  U.S.S.R. .

*Primary Examiner*—Michael Powell Buiz
*Assistant Examiner*—William W. Lewis
*Attorney, Agent, or Firm*—Michael E. Klicpera

[57] ABSTRACT

A device for incising and dilating a stenosis in a vessel of a patient includes a dilator housing and a plurality of blades which can be selectively extended from the housing. Specifically, the housing is formed to surround a chamber and the chamber contains an inflatable balloon. The plurality of blades are formed to have a falciform shape with a curving cutting edge and a similar, curving inner edge. The blades are mounted on the inflatable balloon and pass through slits in the housing. The housing is attached to a placement catheter which includes a lumen for inflating and deflating the balloon. In the operation of the device, the balloon is selectively inflated within the chamber to move the device between a retracted and an expanded configuration. In the retracted configuration, the balloon is deflated and the blades are withdrawn into the housing and the housing is used as a dilator. In the expanded configuration, the balloon is inflated and the blades are extended through the slits in the housing and the device is used as a combination incisor/dilator.

20 Claims, 2 Drawing Sheets

UNIVERSITY DILATOR WITH EXPANDABLE INCISOR

This is a continuation-in-part patent application of U.S. patent application Ser. No. 08/559,415, filed on Nov. 15, 1995, and entitled "Universal Dilator with Expandable Incisor," now U.S. Pat. No. 5,697,944.

FIELD OF THE INVENTION

The present invention pertains generally to cardiovascular surgical tools. More particularly, the present invention pertains to surgical tools which are useful for clearing a stenosis from a vessel of a patient. The present invention is particularly, but not exclusively, useful as a mechanical dilator which can be selectively altered in its configuration to create incisions in a stenosis as the dilator is being distally advanced through the stenosis.

BACKGROUND OF THE INVENTION

Stenotic segments in the vessels and arteries of a patient can develop for many different reasons and can have different adverse effects on the patient. Such segments may occur within multiple vessels of the same organ or may occur as a series of segments within the same vessel. Depending on the location of the particular stenosis, the patient can experience cardiac arrest, stroke, or tissue and organ necrosis. Further, the severity of damage to the patient will, at least to some extent, depend on the nature of the stenosis and the extent of its development. Suffice it to say, stenotic segments can develop throughout a patient's cardiovascular system, and can vary in size, shape and composition. Consequently, they vary in the degree to which they occlude blood flow through the vessel.

A stenosis in a vessel can be quite extensive and occlude a substantial length of a vessel. On the other hand, some stenoses are quite short. Further, some stenoses are highly calcified while other are not. The consequence is that, depending on the nature of the particular stenosis, some surgical tools and procedures are more appropriate than others for clearing the stenosis.

Angioplasty is one of several types of medical procedures which has been widely used in recent years to surgically clear a stenosis in a vessel. More specifically, in an angioplasty procedure, a balloon is placed across the stenosis where it is inflated to dilate the stenosis.

Atherectomy is another type of medical procedure which, as an alternative to angioplasty, has been an acceptable and widely used procedure for surgically clearing a stenosis from a vessel. Quite unlike an angioplasty procedure, however, an atherectomy procedure results in the clearing of the vessel by cutting and removing the stenotic plaque from the vessel.

Still another type medical procedure, though somewhat like angioplasty in its effect on the stenosis, is a dilatation probe. For a procedure using a dilatation probe, the probe is positioned at the site of the stenosis. The probe is then pushed or urged through the stenosis, dilating the stenosis. In an aggressive procedure, the probe can be moved back and forth through the stenosis. In any event, due to the dilating or spreading effect of the probe, the stenosis can be reduced or cleared. Further, in comparison with either an angioplasty or an atherectomy procedure, the use of a dilatation probe is relatively simple.

It has been determined that the dilatation of a stenosis is greatly facilitated if the stenosis is incised before the dilatation. Consequently, several devices have been proposed for this purpose. For example, U.S. Pat. No. 4,273,128 which issued to Lary for an invention entitled "Coronary Cutting and Dilating Instrument" discloses a serial combination of a distal longitudinal incisor and a proximal dilatation balloon. Further, U.S. Pat. No. 5,320,634 which issued to Vigil et al. for an invention entitled "Balloon Catheter with Seated Cutting Edges" discloses a device in which the incising blades are carried on the surface of the angioplasty balloon. Both of these patents are assigned to the same assignee as the present invention and both are incorporated herein by reference.

There is, of course, an ever present danger when sharp instruments are inserted into and through a vessel of a patient to incise tissue. Very importantly, the incising instrument, i.e., a sharpened blade, should be covered during its insertion into the vessel in order to protect the vessel from inadvertent incisions. As a result, it is customary to shield the incising instrument within a hollow catheter until it has reached the area to be treated. Such protection becomes increasingly more important as the distance for travel of the incising instrument through the vessel increases.

The present invention recognizes that an incisor/dilator surgical tool may be well suited for certain procedures. Several factors, however, need to be considered when determining the most desirable structure for an incisor/dilator surgical tool and its method of use. First, it happens that angioplasty and atherectomy procedures may be performed in the coronary arteries, the carotid arteries, the renal arteries, and in the peripheral arteries. Each set of arteries is different and presents different challenges to the angioplasty or atherectomy procedure.

Further, there is the need to satisfy the personal preferences of the particular surgeon who is to perform the atherectomy operation. Clearly, different surgeons can have different approaches to the solution of the same problem. With all of this in mind, there is the need to provide a structure which is best suited and configured for performance of the particular task. The present invention provides such a structure for consideration and use by the operating physician.

In light of the above, it is an object of the present invention to provide a surgical tool which is well suited for use with a number of alternate treatments of a stenotic segment. Another object of the present invention is to provide a surgical tool which protects against inadvertent incision, during transit of the tool through an artery, vessel or any other conduit. Yet another object of the present invention is to provide a surgical tool that is able to treat greater distances than present medical tools and which is capable of treating the entire length of the major coronary arteries and the major branches. Still another object of the present invention is to provide a surgical tool which is relatively easy to manufacture, is simple to operate and is comparatively cost effective.

SUMMARY

The present invention is a device for incising and dilating a treatment area, e.g., a stenosis, in a vessel of a patient. Structurally, the present invention includes a placement catheter having a distal end and a proximal end. The placement catheter is formed with an inflation lumen and is fabricated from a semi-rigid, resilient material which allows the placement catheter to be maneuvered within the vessels of a patient. In particular, a material such as a polyamide, has been found to be appropriate for the placement catheter.

A dilator housing formed to surround a chamber is attached to the distal end of the placement catheter. The dilator housing has a generally ellipsoidal shape chosen for its ability to dilate a stenosis as the dilator housing is either advanced or withdrawn through the stenosis. A cylindrical projection is attached to the distal end of the dilator housing to pre-dilate the stenotic tissue as the dilator housing is advanced. The dilator housing is formed to include a series of longitudinally oriented slits which are distributed radially around the dilator housing. The slits are dimensioned to partially span the length of the dilator housing, starting near the housing's distal end and ending midway between the housing's distal and proximal ends.

An inflatable balloon is positioned inside of the chamber formed within the dilator housing and connected to the inflation lumen of the placement catheter. Functionally, fluid may be passed through the inflation lumen of the placement catheter to selectively inflate or deflate the balloon. The balloon is preferably made of polyethylene, nephalate or PET.

The present invention also includes a plurality of blades. Each blade is formed to have a curved, falciform shape and has an inner edge and an outer cutting edge. The blades are preferably formed from a metal material, such as stainless steel, and each cutting edge is preferably sharpened. Each blade is mounted to the surface of the inflatable balloon and aligned with one of the slits included in the housing. As a result, the balloon may be selectively inflated to move the device between a first configuration, where each blade is contained within the chamber of the housing, and a second configuration where each blade extends radially from the surface of the housing through a respective slit.

Importantly, in the extended configuration, each blade is dimensioned to exceed the greatest diameter of the housing by a distance which is approximately one-half of the thickness of the vessel wall where the device is to be deployed to prevent the blades from cutting completely through the vessel wall.

In cases where it may be desirable to use the present invention in combination with a guidewire, the housing and placement catheter may be formed to include a guidewire lumen.

Operationally, the device of the present invention is first positioned within a vessel of a patient, near the location of the stenosis to be treated. Generally, this is accomplished by first advancing a guidewire through the site of the target stenosis and then advancing the device of the present invention over the guidewire until the stenosis is reached. Once positioned, the device of the present invention may be further advanced to pass the dilator housing through the stenosis. As the dilator housing passes through the stenosis, the stenosis is dilated by the ellipsoidally shaped housing. The dilation procedure may be repeated by retracting, rotating, and readvancing the housing in a reciprocal motion.

To enhance the dilation procedure just described, fluid may be passed through the inflation lumen of the placement catheter inflating the balloon contained within the housing. The inflating balloon moves each of the blades, causing the device to adopt the second configuration where each blade extends radially from the surface of the housing. In this configuration, the device acts as an incisor as well as a dilator, cutting the material of the stenosis as the stenosis is dilated. The degree to which the device acts as an incisor is variable by increasing or decreasing the degree to which the balloon is inflated, thereby selectively controlling the degree to which each blade projects from the housing. To further enhance the dilation procedure, the apparatus may have a reciprocating to and fro motion which would enhance the cutting effect of the blades.

To complete the procedure, fluid is withdrawn from the inflation lumen, deflating the balloon. As the balloon deflates, the device adopts the first configuration where each of the blades is contained within the housing. The device of the present invention, along with the guidewire, may then be withdrawn from the patient. During withdrawal, inadvertent contact between the blades and the patient is prevented by the position of the blades within the dilation housing.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
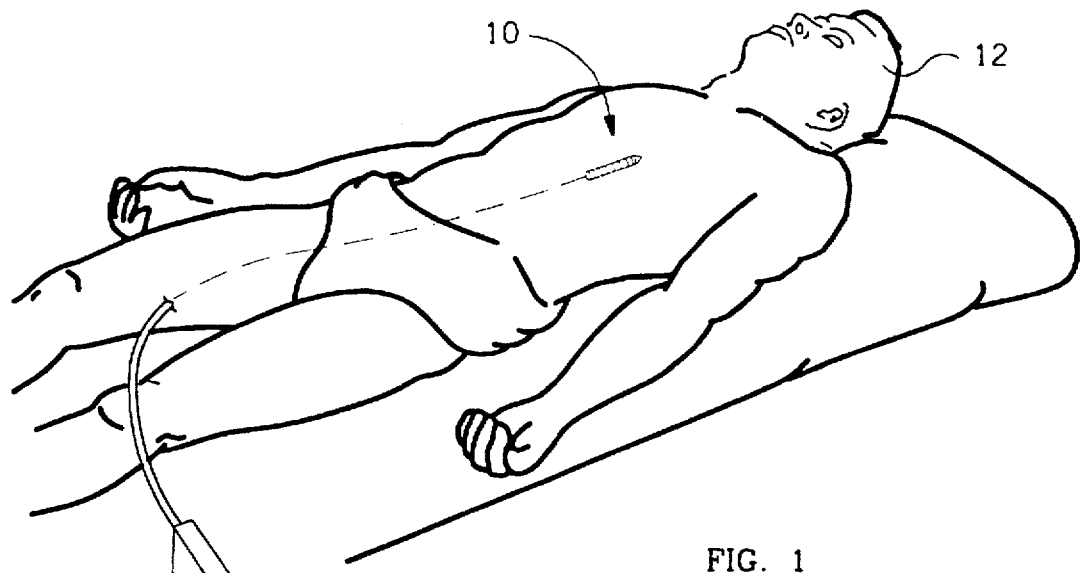
FIG. 1 is a view of a patient and the intended environment for operation of a surgical dilator tool with expandable incisors of the present invention.

Referring initially to FIG. 1, a device for incising and dilating a treatment area, e.g., a stenosis, within a vessel is shown and generally designated 10. More specifically, the device 10 is shown positioned in the artery of a patient 12. As will be appreciated by the skilled artisan, the device 10 is shown schematically positioned in the patient 12, and it is to be understood that use of the device 10 is not confined to only upper body arteries and vessels but, instead, can be used in arteries and vessels throughout the patient 12.

Figure 2:
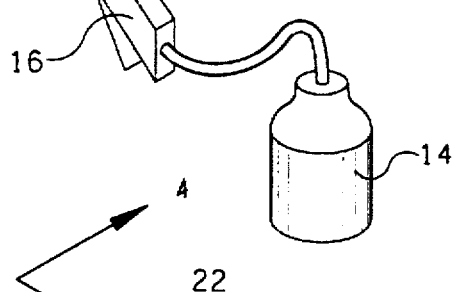
FIG. 2 is an isometric view of the surgical dilator tool with expandable incisors of the present invention shown in a retracted configuration.
Figure 3:
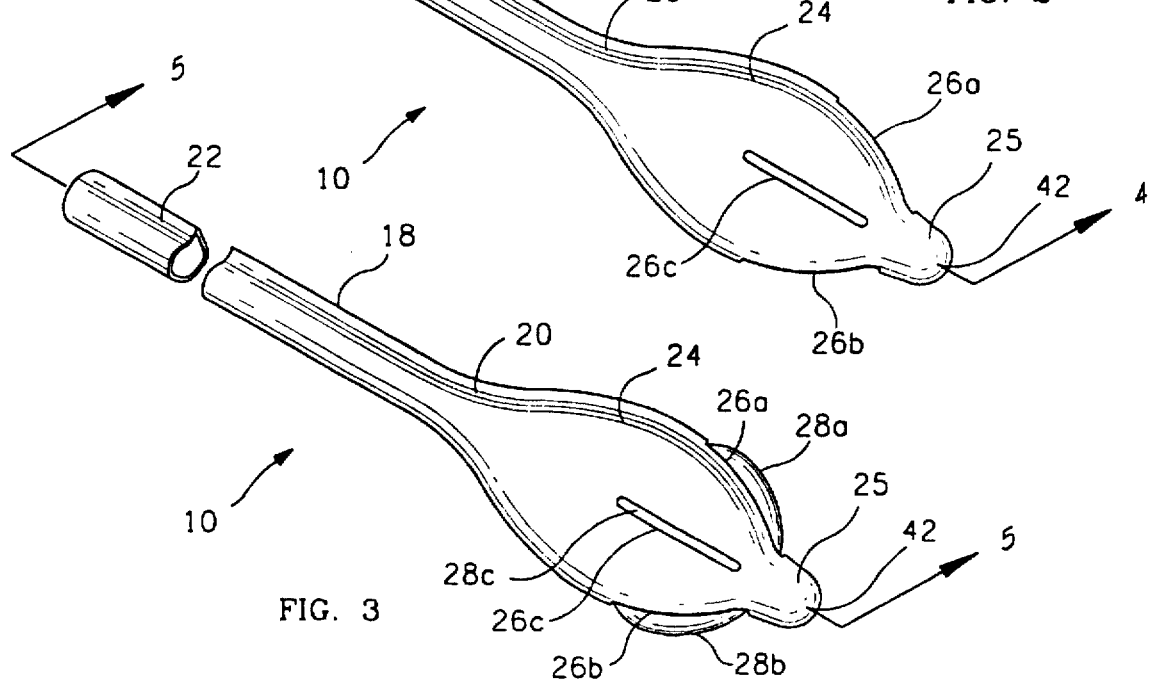
FIG. 3 is an isometric view of the surgical dilator tool with expandable incisors of the present invention shown in an expanded configuration.

Referring now to FIGS. 2 and 3, it may be seen that the device 10 of the present invention includes a placement catheter 18 having a distal end 20 and a proximal end 22. The placement catheter 18 is formed from a resilient and flexible material, such as a polyamide, allowing the placement catheter 18 to be maneuvered within the vascular system of the patient 12. A rigid dilator housing 24 is attached to the distal end 20 of the placement catheter 18 and has a generally ellipsoidal shape. Functionally, the ellipsoidal shape allows the dilator housing 24 to dilate a stenosis as the dilator housing 24 is either advanced or withdrawn through a stenosis.

With specific reference to FIG. 2, it may be seen that the housing 24 is formed to include a series of slits 26, of which slit 26a and 26b are exemplary. The slits 26 are distributed radially around the housing 24 and each slit 26 is oriented to substantially follow the longitudinal axis of the dilator housing 24. Each slit 26 is dimensioned to partially span the length of the dilator housing 24, starting at the distal end of the dilator housing 24 and ending midway between the distal and proximals ends of the dilator housing 24.

With reference now to FIG. 3, it may be seen that the present invention includes a series of blades 28 of which blade 28a and 28b are exemplary. Each blade 28 has a generally curving falciform, or sickle, shape and projects radially from a respective slit 26. Like the slits 26, each blade 28 is oriented to substantially follow the longitudinal axis of the dilator housing 24 and placement catheter 18.

Preferably, the device 10 includes a cylindrical projection 25 that is attached to the distal end of the dilator housing 24 to pre-dilate the stenosis as the dilator housing 24 is advanced. The pre-dilation of the stenosis allows the blades 28 to contact the stenotic wall. The dilator housing 24 and projection 25 can be formed from a single piece of a hard, rigid, plastic such as ABS.

As clearly demonstrated by comparison of FIGS. 2 and 3, the device 10 of the present invention is capable of two distinct configurations. In the first configuration, shown in FIG. 2, the device 10 is configured as a dilation tool. When so configured, the device 10 may be advanced or withdrawn through a stenosis to mechanically dilate the stenosis. Alternatively, in the second configuration shown in FIG. 3, the device 10 of the present invention is configured as a combined dilator/incisor. In this configuration, the device 10 may be advanced or withdrawn through a stenosis to mechanically incise and dilate the stenosis.

Figure 4:
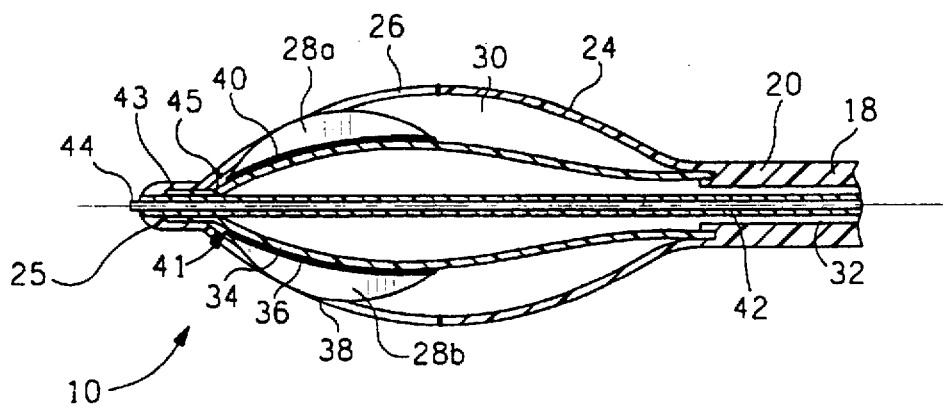
FIG. 4 is cross-sectional view of the surgical dilator tool with expandable incisors of the present invention taken along the line marked 4—4 in FIG. 2.
Figure 5:
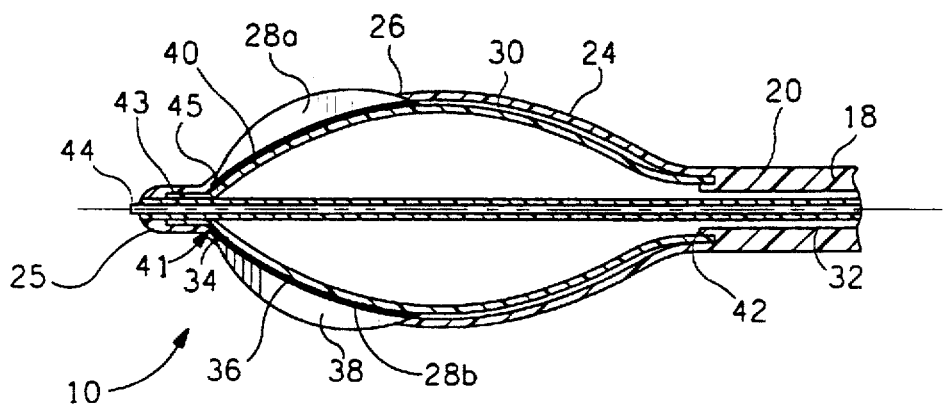
FIG. 5 is cross-sectional view of the surgical dilator tool with expandable incisors of the present invention taken along the line marked 5—5 in FIG. 3.

The structural details that allow the present invention to move between the first configuration of FIG. 2 and the second configuration of FIG. 3 are best appreciated by reference to FIGS. 4 and 5. In FIG. 4 and 5, it may be seen that the dilator housing 24 is formed to surround a chamber 30. Additionally, it may be seen that the placement catheter 18 is formed to surround an inflation lumen 32. An inflatable balloon 34 is positioned inside of the dilator housing and attached in fluid communication with the inflation lumen 32 of the placement catheter 18. In this fashion, fluid may be selectively passed through the inflation lumen 32 to selectively inflate the balloon 34.

FIGS. 4 and 5 also show that each blade 28 is formed with an inner edge 36 and an opposite cutting edge 38. Preferably, both the inner edge 36 and cutting edge 38 are curved, with the curve of the cutting edge 38 chosen to substantial match the contour of the dilator housing 24. The combination of the curved inner edge 36 and cutting edge 38 gives the blades 28 a substantially falciform, or sickle, shape. Each blade 28 is also dimensioned to ensure that the cutting edge 38 is substantially within its respective slit 26 when the device 10 is positioned in the first configuration shown in FIGS. 2 and 4.

A basal strip 40 is attached to the inner edge of each blade 28 giving the blade 28 an inverted T-shaped cross-section. The basal strip 40 of each blade 28 is attached to the surface of the inflatable balloon 34 using a suitable adhesive. As a result, each blade 28 moves with the balloon 34 as the balloon 34 is selectively inflated. In this fashion, each blade 28 may be moved between the first configuration, shown in FIGS. 2 and 4, and the second configuration shown in FIGS. 3 and 5 by inflation or deflation of the balloon 34. As the blades 28 move between the first and second configurations, each slit 26 provides a guide, directing the movement of the corresponding blade 28. Each slit 26 is also dimensioned to prevent passage of the basal strip 40. As a result, should the blade 28 become detached from the balloon 34, the blade 28 will be safely trapped within dilator housing 24. Importantly, when the device is caused to adopt the second configuration of FIGS. 3 and 5, each blade 28 is dimensioned so that the blade 28 exceeds the greatest diameter of the dilator housing 24 housing by a distance which is approximately one-half of the thickness of the vessel wall where the device is to be deployed.

Preferably, the device 10 includes a blade support 41 which secures the blades 28 to the dilator housing 24 and additionally supports the blades 28. In the embodiment shown in the Figures, the blade support 41 includes a tubular section 43 and a plurality of flexible tabs 45. Referring to FIGS. 4 and 5, the tubular section 43 is disposed in and is securely retained in the cylindrical projection 25. Each flexible tab 45 projects from the tubular section 43 and secures one of the blades 28 to the tubular section 43. In this embodiment, the movement of the balloon 34 causes the blades 28 to move and the flexible tabs 45 to deflect. Preferably, the flexible tabs 45 are bias to return the blades 28 to substantially within the dilator housing 24 so that blades 28 may return within the dilator housing 24 even if the blades 28 become detached from the balloon 34. The tubular section 43 and the flexible tabs 45 can be formed from a resilient metallic material such as stainless steel.

To allow the device 10 to be used in combination with a guidewire, the placement guide catheter 18 is formed with a guidewire lumen 42. The guidewire lumen 42 extends throughout the placement catheter 18 and terminates at the distal end of the dilation housing 24. For the purposes of the present invention, the guidewire lumen 42 is dimensioned to receive a guidewire 44.

Preferably, the cylindrical projection 25, the blades 28 and the dilation housing 24 include a low friction, heparin surface to reduce trauma to the vessel and to slow clotting or coagulating of the blood. A suitable surface treatment can be provided by the company BSI of Eden Prairie, Minn.

OPERATION

Figure 6:
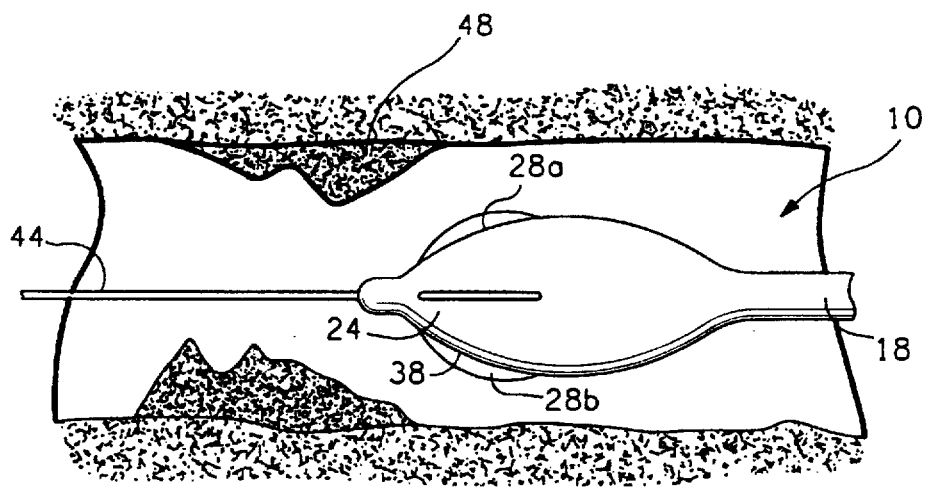
FIG. 6 is a plan view of the present invention operationally positioned within a vessel of a patient.

As best appreciated by reference to FIG. 6, operation of the device 10 of the present invention begins by prepositioning the guidewire 44 in the vessel 46 of patient 12. In this fashion, guidewire 44 establishes a pathway to and through the stenotic segment 48 which is to be dilated. The device 10 is then inserted over the guidewire 44 by passing the guidewire 44 through the guidewire lumen 42 of the device 10. The device 10 is then advanced over the guidewire 44 to position the dilation housing 24 at the site of the stenotic segment 48. During the advancement of device 10 over guidewire 44, the device 10 is preferably configured in the first configuration (shown in FIGS. 2 and 4). In this configuration the balloon 34 is deflated and the blades 28 are withdrawn into the chamber 30. In this manner, inadvertent contact between the blades 28 and the vessel 46 is prevented.

Once the dilation housing 24 of device 10 is positioned at the site of the stenotic segment 48, an inflator 16 may be used to activate the fluid supply 18 to pass fluid under pressure through the inflation lumen 32 to inflate the balloon 34. The inflation of the balloon 34 causes the device 10 to adopt the second configuration with the blades 28 extended radially from the dilator housing 24 through the slits 26. Consequently, any further movement of device 10 along guidewire 44 will cause the blades 28 to incise the stenosis 48. This incision is accompanied by a dilatation of the stenosis 48 caused by the simultaneous advancement of the dilation housing 24.

It is to be appreciated that device 10 can be manipulated back and forth in the distal and proximal directions through the stenosis 48 as desired. Thus, incision and dilatation of the stenotic segment 48 can be as aggressive as is required. A rapid to and fro reciprocating action combined with slight pressure can be used to assist the cutting action of the blades. Further, as deemed necessary, the inflator 16 may be manipulated to pass fluid into balloon 34 to selectively increase or decrease the extension of the blades 28. Thus, the extension of the blades 28 from housing 24 can be varied to configure device 10 as an incisor/dilator having different incising capabilities.

It is also to be appreciated that since the device 10 can operate as a dilator or alternately, as an incisor, the device is capable of treating the entire length of the major coronary arteries and the major branches.

While the particular surgical dilator tool with expandable incisors herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A device for incising and dilating a treatment area in a vessel which comprises:
    an inflatable balloon having an outer surface;
    at least one blade having an inner edge and a cutting edge, said blade being moveable with said balloon with said cutting edge extending from said balloon;
    a substantially ellipsoidal shaped housing having a slit for the blade, said housing surrounding a chamber, said balloon being positioned in said chamber with said blade aligned with the slit; and
    an inflator for selective inflation of said balloon in said chamber to move the blade between a first position wherein the blade is substantially withdrawn into said housing and a second position wherein the blade at least partly extends through the slit of said housing.

2. A device as recited in claim 1 further comprising a cylindrical projection attached to the distal end of said housing.

3. A device as recited in claim 1 comprising a placement catheter extending through said balloon and a guidewire insertable through said catheter, said guidewire being prepositionable in the vessel for advancing said device to the treatment area in the vessel.

4. A device as recited in claim 1 wherein said blade is made of a metal.

5. A device as recited in claim 1 wherein said housing is made of a substantially rigid plastic.

6. A device for incising and dilating a treatment area in a vessel which comprises:
    an inflatable balloon;
    a plurality of substantially falciform shaped blades, each said blade having an inner edge and a curved cutting edge, said inner edge of each said blade attached to said balloon;
    means for dilating said treatment area in said vessel, said dilating means shaped to surround said balloon; and
    an inflator for inflating said balloon between a first position wherein said blades are substantially withdrawn into said dilating means for use of said device as a dilator and a second position wherein said blades at least partly extend from said dilating means for use of said device as an incisor.

7. A device as recited in claim 6 wherein said blades are made of a metal.

8. A device as recited in claim 6 wherein said dilating means comprises a housing defining an interior chamber, the housing having a plurality of slits therethrough, said balloon being positioned in said chamber with said blades aligned with said slits.

9. A device as recited in claim 6 wherein said housing is substantially ellipsoidal in shape.

10. A device as recited in claim 9 further comprising a cylindrical projection attached to the distal end of said housing.

11. A device as recited in claim 6 wherein said housing is made of a substantially rigid plastic.

12. A device as recited in claim 6 comprising a placement catheter, said placement catheter being formed with a lumen and having a distal end, said distal end of said placement catheter being attached to said housing for positioning of said housing in said vessel.

13. A device as recited in claim 12 wherein said balloon and said placement catheter are formed with a lumen for receiving a guidewire.

14. A device as recited in claim 6 wherein said balloon is made of PET.

15. A device for incising and dilating a treatment area in a vessel which comprises:
    an inflatable balloon having an outer surface;
    at least one blade having an inner edge and a cutting edge, said blade being moveable with said balloon with said cutting edge extending from said balloon;
    a housing having a slit for the blade, said housing surrounding a chamber, said balloon being positioned in said chamber with said blade aligned with the slit;
    an inflator for selective inflation of said balloon in said chamber to move the blade between a first position wherein the blade is substantially withdrawn into said housing and a second position wherein the blade at least partly extends through the slit of said housing; and
    a strip secured proximate to the inner edge of the blade, the strip being shaped to prevent passage of the strip through the slit.

16. The device of claim 15 wherein the housing is substantially ellipsoidal shaped.

17. A method for incising and dilating a treatment area in a vessel of a patient which comprises the steps of:
    advancing a device through the vessel to proximate the treatment area, said device comprising an inflatable balloon, at least one blade, the blade having an inner edge and a cutting edge, said inner edge of said blade mounted on said balloon, a housing formed with a slit for each blade to surround a chamber therein, said balloon being positioned in said chamber with the blade aligned with the slit;
    selectively inflating said balloon to extend said blade at least partly through said slit of said housing to incise said stenosis;
    selectively deflating said balloon to at least partly withdraw said blade into said housing; and
    moving said housing of said device in the vessel and through the treatment area to dilate the treatment area.

18. A method as recited in claim 17 wherein advancing step is accomplished by the steps of:
    prepositioning a guidewire in the vessel and through the treatment area; and
    inserting said guidewire into said lumen; and
    advancing said balloon over said guidewire until the balloon is proximate the treatment area.

19. A method as recited in claim 18 further comprising the steps of:
    prepositioning a guide catheter in the vessel, said guide catheter being formed with a lumen for receiving said housing to guide said housing to the stenosis; and
    advancing said housing through said lumen of said guide catheter until the housing is proximate the treatment area.

20. The method of claim 17 wherein the step of moving said housing also includes the step of selectively inflating said balloon to extend said blade at least partly through said slit of said housing.

* * * * *

UNITED STATES PATENT AND TRADEMARK OFFICE
CERTIFICATE OF CORRECTION

PATENT NO. : 5,792,158
DATED : August 11, 1998
INVENTOR(S) : Lary

It is certified that error appears in the above-identified patent and that said Letters Patent is hereby corrected as shown below:

Title of Invention: Replace the word "University" with "Universal"

Signed and Sealed this

Fifteenth Day of May, 2001

*Attest:*

NICHOLAS P. GODICI

*Attesting Officer*     Acting Director of the United States Patent and Trademark Office